United States Patent

Winstanley et al.

[11] Patent Number: 5,900,398
[45] Date of Patent: May 4, 1999

[54] SULFATED/SULFONATED SURFACTANTS

[75] Inventors: Richard A. Winstanley, Broad Axe; Harald P. Wulff, Bryn Mawr, both of Pa.

[73] Assignee: Henkel Corporation, Gulph Mills, Pa., PA

[21] Appl. No.: 09/025,488

[22] Filed: Feb. 18, 1998

Related U.S. Application Data

[62] Division of application No. 08/647,611, May 13, 1996, Pat. No. 5,780,421
[60] Provisional application No. 60/012,829, Mar. 5, 1996.
[51] Int. Cl.⁶ ...................................................... C11D 1/83
[52] U.S. Cl. ............................................. 510/429; 510/428
[58] Field of Search ................................... 510/126, 127, 510/237, 351, 352, 470, 494, 495, 357, 358, 426, 427, 428, 429, 472

[56] References Cited

U.S. PATENT DOCUMENTS

| | | | |
|---|---|---|---|
| 4,597,770 | 7/1986 | Forand et al. | 44/51 |
| 4,609,478 | 9/1986 | Egan | 252/8.55 D |
| 4,973,686 | 11/1990 | Kretschmann et al. | 536/118 |
| 5,312,934 | 5/1994 | Letton | 554/98 |
| 5,429,684 | 7/1995 | Osberghaus et al. | 134/3 |
| 5,431,780 | 7/1995 | Raehse et al. | 159/48.1 |
| 5,478,930 | 12/1995 | McCurry, Jr. et al. | 536/18.6 |
| 5,516,447 | 5/1996 | Bauer et al. | 252/89.1 |
| 5,523,016 | 6/1996 | Giesen et al. | 252/174.17 |

*Primary Examiner*—Paul Lieberman
*Assistant Examiner*—John R. Hardee
*Attorney, Agent, or Firm*—Ernest G. Szoke; Wayne C. Jaeschke; Steven J. Trzaska

[57] ABSTRACT

A process for making a surfactant product involving the steps of: (1) providing a solid water-free sugar surfactant; (2) providing a co-reactant selected from the group consisting of alpha-olefins, internal olefins, linear alkylbenzene, branched alkylbenzene, fatty alcohol, alkoxylated fatty alcohol, secondary alkanes, N-methylglucamide, tall oil, napthalene, xylene, cumene, toluene, dodecylbenzene and mixtures thereof; (3) dispersing or dissolving the solid water-free sugar surfactant in the co-reactant to form a feed mixture; and (4) sulfating/sulfonating the feed mixture to form a surfactant product.

9 Claims, No Drawings

SULFATED/SULFONATED SURFACTANTS

CROSS-REFERENCE TO RELATED APPLICATIONS

This application claims priority from U.S. provisional application Serial No. 60/012,829, filed Mar. 5, 1996, the disclosure of which is incorporated herein by reference. This application is a divisional of Ser. No. 08/647,611, filed May 13, 1996, now U.S. Pat. No. 5,780,421.

FIELD OF THE INVENTION

The present invention generally relates to a novel surfactant and process for making same. More particularly, it has been surprisingly found that an anionic/nonionic surfactant mixture having enhanced surface-active properties can be obtained by co-sulfating/sulfonating a solid-form nonionic sugar surfactant.

BACKGROUND OF THE INVENTION

Sugar surfactants, for example alkyl oligoglucosides or fatty acid-N-alkyl glucamides, are distinguished by excellent detergent properties and high ecotoxicological compatibility. For this reason, these classes of nonionic surfactants are acquiring increasing significance. They are generally used in liquid and powder formulations, for example laundry and dishwashing detergents and hair shampoos. However, because of their increased desirability as surface active agents, their use as surfactants in many other types of products is growing rapidly.

While conventional sugar surfactants perform satisfactorily in many applications, there is a constant need to both enhance and expand their performance properties. Methods of improving the performance of conventional sugar surfactants by increasing: their foaming and foam stability, tolerance to water hardness and detergency, continue to be sought. Moreover, the use of sugar surfactants in topical skin products also requires a reduction in their tendency towards skin and eye irritation.

SUMMARY OF THE INVENTION

The present invention provides a novel surfactant product formed by a process involving the steps of:

(1) providing a solid water-free sugar surfactant;

(2) providing a co-reactant selected from the group consisting of alpha-olefins, internal olefins, linear alkylbenzene, branched alkylbenzene, fatty alcohol, alkoxylated fatty alcohol, secondary alkanes, N-methylglucamide, tall oil, napthalene, xylene, cumene, toluene, dodecylbenzene, and mixtures thereof;

(3) dispersing or dissolving the sugar surfactant in the co-reactant to form a feed mixture; and (4) sulfating/sulfonating the feed mixture to form a surfactant product.

The present invention is also directed to a surfactant composition containing:

(a) an unreacted solid water-free sugar surfactant;

(b) an unreacted co-reactant selected from the group consisting of alpha-olefins, internal olefins, linear alkylbenzene, branched alkylbenzene, fatty alcohol, alkoxylated fatty alcohol, secondary alkanes, N-methylglucamide, tall oil, napthalene, xylene, cumene, toluene, dodecylbenzene, and mixtures thereof;

(c) a sulfated/sulfonated derivative of the solid water-free sugar surfactant of component (a); and (d) a sulfated/sulfonated derivative of the co-reactant of component (b).

DESCRIPTION OF THE INVENTION

Other than in the operating examples, or where otherwise indicated, all numbers expressing quantities of ingredients or reaction conditions used herein are to be understood as being modified in all instances by the term "about".

The novel surfactant mixture of the present invention is derived from the co-sulfation/sulfonation of nonionic sugar surfactants. Suitable nonionic sugar surfactants include, but are not limited to alkyl and alkenyl oligoglycosides and fatty acid N-alkyl polyhydroxyalkylamides. Alkyl and alkenyl oligoglycosides are known nonionic surfactants corresponding to general formula (I):

$$R^1O\text{---}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl polyglycosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl polyglycosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty acid N-alkyl polyhydroxyalkylamides are nonionic surfactants corresponding to formula (II):

in which $R^2CO$ is an aliphatic acyl radical containing 6 to 22 carbon atoms, $R^3$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride.

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (III):

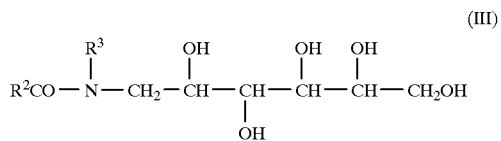

Preferred fatty acid N-alkyl polyhydroxyalkylamides are glucamides corresponding to formula (III) in which $R^3$ is hydrogen or an alkyl group and $R^2CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (III) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

Commercially available sugar surfactants, such as those listed above, are offered in aqueous form and contain certain levels of both water and contaminants. While this form is generally acceptable in most formulation cases, it is unacceptable for purposes of the present invention. The presence of water and contaminants in these types of aqueous sugar surfactants results in the formation of unwanted sulfuric and/or hydrochloric acid and other degradation products because of the contaminants' reactivity during the sulfation/sulfonation process. Thus, the sugar surfactants used as starting materials for the present invention must possess very low levels of degradation (contamination) and little, if any, water.

Moreover, it is preferred that the solid water-free sugar surfactants, in powder or granular form, also possess an apparent density above 500 g/l.

Due to the above-identified disadvantages associated with the use of commercially available aqueous sugar surfactants, the present invention employs a solid water-free sugar surfactant, preferably in either powder or granular form, which is also referred to as a flash dried sugar surfactant.

One example of how such solid water-free (flash dried) sugar surfactants can be produced involves the simultaneous drying and granulating of water-containing pastes of sugar surfactants. The simultaneous drying and granulation process takes place in a horizontally arranged thin-layer evaporator with rotating fittings of the type marketed, for example, by the VRV company under the name of "flash dryer". In simple terms, the flash dryer is a tube which can be heated to different temperatures over several zones. The paste-form starting material, which is introduced by a pump, is projected onto the heated wall by one or more shafts fitted with paddles or plowshares as rotating fittings and is dried on the heated wall in a thin layer typically with the thickness of 1 to 10 mm. According to the invention, it has been found to be of advantage to apply a temperature gradient of 170° C. (product entrance) to 20° C. (product exit) to the thin layer evaporator. To this end, the first two zones of the evaporator for example may be heated to 160° C. and the last zone to 20° C. Higher drying temperatures have not been found to be of advantage in view of the thermal lability of the starting materials. The thin-layer evaporator is operated at atmospheric pressure. Air is passed through in countercurrent (throughput 50 to 150 m³/h). The gas entry temperature is generally in the range from 20 to 30° C. while the exit temperature is in the range from 90 to 110° C.

The water-containing sugar surfactant pastes which may be used as starting materials may have a solids content above 20% by weight and preferably in the range from 25 to 75% by weight. Typically, their solids content is of the order of 30 to 50% by weight. The throughput is of course dependent on the size of the dryer, but is typically in the range from 5 to 15 kg/h. It is advisable to heat the pastes to 40 to 60° C. during their introduction.

In addition, after drying, it has proved to be of considerable advantage to transfer the granules, which still have a temperature of around 50 to 70° C., to a conveyor belt, preferably in the form of a vibrating shaft, and rapidly to cool them thereon, i.e. over a period of 20 to 60 seconds, to temperatures of around 30 to 40° C. using ambient air. In order to further improve their resistance to the unwanted absorption of water, the granules may also be subsequently dusted with 0.5 to 2% by weight of silica powder.

It should be noted that while the above-described process of forming suitable solid water-free (flash dried) sugar surfactants is exemplified, any other method of forming solid sugar surfactants which are substantially both water- and contaminant-free, i.e., containing little, if any, water and contaminants, may be employed without departing from the spirit of the invention.

The flash dried sugar surfactant starting materials, substantially free of both water and contaminants, are then dispersed or dissolved in a co-reactant to form a feed mixture. Examples of suitable co-reactants include, but are not limited to, alpha-olefins, internal olefins, linear alkylbenzene, branched alkylbenzene, fatty alcohols, alkoxylated fatty alcohols, secondary alkanes, N-methylglucamides, tall oil, napthalene, xylene, cumene, toluene, dodecylbenzene, and mixtures thereof. A particularly preferred co-reactant is an alkoxylated fatty alcohol. In general, the mixture feed should contain a sugar surfactant solids content ranging from about 0.5 to about 99.5% by weight, based on the weight of the mixture feed.

Once the mixture feed is formed, it is then subjected to a sulfation/sulfonation process. The sulfation and/or sulfonation of organic compounds is well known in the art. There are primarily two types of reactions between an organic compound and sulfuric acid reactants: sulfation which produces sulfates having C—OS— linkages, and sulfonation which produces sulfonates having C—S linkages.

The sulfation/sulfonation process generally involves reacting the organic compound to be sulfated and/or sulfonated with either concentrated sulfuric acid/oleum, chlorosulfonic acid or sulfurtrioxide. The type of equipment and specific reaction conditions associated therewith which are employed to perform this process are well known in the art, an example of which is U.S. Pat. No. 4,973,686 issued to Henkel KGaA on Nov. 27, 1990, the entire contents of which are incorporated herein by reference.

The resultant surfactant product formed by the above-disclosed process contains a mixture of unreacted water-free sugar surfactant, unreacted co-reactant, sulfated and/or sulfonated derivatives of the water-free sugar surfactant, and sulfated and/or sulfonated derivatives of the co-reactant, all of which comprise the surfactant product.

The surfactant product may subsequently be neutralized, in order to attain a pH ranging from about 5 to about 9, with an alkali material in order to form a neutralized final surfactant product. Suitable alkali materials include, but are not limited to, sodium hydroxide, magnesium hydroxide, calcium hydroxide, TEA, and the like. It is this final surfactant product which possesses both anionic and nonionic surfactant characteristics, thereby imparting improved surface active properties, enhanced levels of foaming and foam stability, better detergency, and increased water solubility, onto products utilizing it as a surfactant component in their formulation.

The particular amount of surfactant product to be used in formulating a cleaning composition, whether it be a laundry detergent, dishwashing detergent, hair shampoo and the like, will be easily determined by those skilled in the formulation of a specific cleaning composition.

EXAMPLE

A sulfonated/sulfated surfactant in accordance with the present invention can be formulated by mixing about 75% by weight of a solid, water-free, i.e., flash dried, alkyl polyglycoside with about 25% by weight of an alkoxylated fatty alcohol to form a feed mixture. The feed mixture can then be sulfated/sulfonated by reacting the feed mixture with sulfurtrioxide to form the novel surfactant composition of the invention.

What is claimed is:

1. A surfactant composition comprising:
   (a) an unreacted water-free sugar surfactant;
   (b) an unreacted co-reactant selected from the group consisting of alpha-olefins, internal olefins, linear alkylbenzene, branched alkylbenzene, secondary alkanes, tall oil, napthalene, xylene, cumene, toluene, dodecylbenzene, and mixtures thereof;
   (c) a sulfated/sulfonated derivative of the water-free sugar surfactant of component (a); and
   (d) a sulfated/sulfonated derivative of the co-reactant of component (b).

2. The composition of claim 1 wherein the solid water-free sugar surfactant of component (a) is selected from the group consisting of alkyl oligoglycosides, alkenyl oligoglycosides, fatty acid N-alkyl polyhydroxyalkylamides and mixtures thereof.

3. The composition of claim 1 wherein the solid water-free sugar surfactant of component (a) has an apparent density above 500 g/l.

4. The composition of claim 2 wherein the solid water-free sugar surfactant of component (a) is a flash dried alkyl oligoglucoside.

5. The composition of claim 2 wherein the solid water-free sugar surfactant of component (a) is a glucamide.

6. A cleaning composition containing an effective amount of a surfactant composition, the surfactant composition comprising:
   (a) an unreacted water-free sugar surfactant;
   (b) an unreacted co-reactant selected from the group consisting of alpha-olefins, internal olefins, linear alkylbenzene, branched alkylbenzene, secondary alkanes, tall oil, napthalene, xylene, cumene, toluene, dodecylbenzene, and mixtures thereof;
   (c) a sulfated/sulfonated derivative of the water-free sugar surfactant of component (a); and
   (d) a sulfated/sulfonated derivative of the co-reactant of component (b).

7. The composition of claim 6 wherein the solid water-free sugar surfactant of component (a) is selected from the group consisting of alkyl oligoglycosides, alkenyl oligoglycosides, fatty acid N-alkyl polyhydroxyalkylamides and mixtures thereof.

8. The composition of claim 6 wherein the solid water-free sugar surfactant of component (a) has an apparent density above 500 g/l.

9. The composition of claim 7 wherein the solid water-free sugar surfactant of component (a) is a flash dried alkyl oligoglucoside.

* * * * *